(12) United States Patent
Yang (10) Patent No.: US 8,735,160 B2
(45) Date of Patent: May 27, 2014

(54) METHODS FOR TARGETTED MUTAGENESIS IN GRAM-POSITIVE BACTERIA

(75) Inventor: Yunfeng Yang, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1167 days.

(21) Appl. No.: 12/233,806

(22) Filed: Sep. 19, 2008

(65) Prior Publication Data

US 2010/0075303 A1 Mar. 25, 2010

(51) Int. Cl.
*C12Q 1/68* (2006.01)
*C12N 15/87* (2006.01)

(52) U.S. Cl.
USPC .......................................... 435/471; 435/440

(58) Field of Classification Search
None
See application file for complete search history.

(56) References Cited

PUBLICATIONS

Yang et al. (Laboratory Directed Research and Development Program FY 2007 Annual Report, Oak Ridge National Laboratory, Mar. 2008, pp. 1-222).*
Alexeyev M. F., "The pKNOCK Series of Broad-Host-Range Mobilizable Suicide Vectors for Gene Knockout and Targeted DNA Insertion into the Chromosome of Gram-Negative Bacteria", *Bio Techniques* 26(5): 824-828 (1999).
Green E. M., et al., "Genetic manipulation of acid formation pathways by gene inactivation in *Clostridium acetobutylicum* ATCC 824", *Microbiology* 142: 2079-2086 (1996).
Harris L. M., et al., "Northern, Morphological, and Fermentation Analysis of *spoOA* Inactivation and Overexpression in *Clostridium acetobutylicum* ATCC 824", *Journal of Bacteriology* 184(13): 3586-3597 (2002).
Mermelstein L. D., et al., "In Vivo Methylation in *Escherichia coli* by the *Bacillus subtillis* Phage ϕ3T I Methyltransferase to Protect Plasmids from Restriction upon Transformation of *Clostridium acetobutylicum* ATCC 824", *Applied and Environmental Microbiology* 59(4): 1077-1081 (1993).
Tummala S. B., et al., "Development and Characterization of a Gene Expression Reporter System for *Clostridium acetobutylicum* ATCC 824", *Applied and Environmental Microbiology* 65(9): 3793-3799 (1999).
Jennert K. C. B., et al., "Gene transfer to *Clostridium cellulolyticum* ATCC 35319", *Microbiology* 146: 3071-3080 (2000).
Kolter R., et al., "Trans-Complementation-Dependent Replication of a Low Molecular Weight Origin Fragment from Plasmid R6K", *Cell* 15: 1199-1208 (1978).
Garcia-Martinez D. V., et al., "Studies on Cellulase Production by *Clostridium thermocellum*", *European J. Appl. Microbiol. Biotechnol.* 9: 189-197 (1980).
Lamed R., et al., "Cellulosomes from *Clostridium thermocellum*", *Methods in Enzymology* 160: 472-482 (1988).
Perret S., et al., "Use of antisense RNA to modify the composition of cellulosomes produced by *Clostridium cellulolyticum*", *Molecular Microbiology* 51(2): 599-607 (2004).
Tardif C., et al., "Electrotransformation studies in *Clostridium cellulolyticum*", *Journal of Industrial Microbiology & Biotechnology* 27: 271-274 (2001).
Béguin P. et al., Chapter 8 Applied Genetics of Anaerobic Thermophiles, Thermophiles General, Molecular, and Applied Microbiology (1986) 179-195.
Beveridge T. J., Ultrastructure, Chemistry, and Function of the Bacterial Wall, International Review of Cytology (1981) 229-317:72.
Lynd L. R. et al., Microbial Cellulose Utilization: Fundamentals and Biotechnology, Microbiology and Molecular Biology Reviews (2002) 506-577:66(3).
Maki M. et al., The prospects of cellulase-producing bacteria for the bioconversion of lignocellulosic biomass, International Journal of Biological Sciences (2009) 500-516:5(5).
Salyers et al., Appendix 1 Cell Surface Structure of Bacteria, Bacterial Pathogenesis a Molecular Approach (1994) 339-342.
Selvaraj G. et al., Suicide Plasmid Vehicles for Insertion Mutagenesis in *Rhizobium meliloti* and Related Bacteria, Journal of Bacteriology (1983) 1292-1300:156(3).

* cited by examiner

*Primary Examiner* — Robert A Zeman
(74) *Attorney, Agent, or Firm* — Scully, Scott, Murphy & Presser, P.C.

(57) ABSTRACT

The present invention provides a method of targeted mutagenesis in Gram-positive bacteria. In particular, the present invention provides a method that effectively integrates a suicide integrative vector into a target gene in the chromosome of a Gram-positive bacterium, resulting in inactivation of the target gene.

19 Claims, 5 Drawing Sheets

| Antibiotic | 0.3x | 1x | 3x | µg/ml (1x) |
|---|---|---|---|---|
| kanamycin | + | + | + | 50 |
| ampicillin | + | + | + | 100 |
| gentamycin | + | + | - | 15 |
| rifampicin | - | - | - | 10 |
| tetracycline | - | - | - | 5 |
| chloramphenicol | - | - | - | 34 |
| thiamphenicol | - | - | - | 10 |
| erythromycin | - | - | - | 10 |

METHODS FOR TARGETTED MUTAGENESIS IN GRAM-POSITIVE BACTERIA

STATEMENT REGARDING FEDERALLY SPONSORED RESEARCH OR DEVELOPMENT

This invention was made with Government support under Contract No. DE-AC05-00OR22725 awarded by the United States Department of Energy. The Government has certain rights in this invention.

FIELD OF THE INVENTION

The present invention generally relates to targeted mutagenesis in Gram-positive bacteria. In particular, the present invention provides a method that utilizes a suicide integrative vector to genetically modify Gram-positive bacteria, especially Gram-positive bacteria within the class of Clostridia.

BACKGROUND OF THE INVENTION

Achieving the national goal of reducing oil imports will require bioenergy production from biomass. Biofuels are secure energy resources because of the domestic and global availability of biomass. Moreover, biofuels are renewable and thereby inexhaustible, expandable to meet the growing demand of national and world economies, and supportable by modern agricultural infrastructure. It has been projected that biological derived energy will make up a substantial portion of future energy use. By 2100, biofuels use could equal all global fossil energy today (8).

The predominant biofuel today is starch-derived ethanol. About 4 billion gallons of ethanol are produced every year, which could displace 2% of fossil fuel consumed (8). However, the expansion of ethanol production from food starch is ultimately limited and has a low 14% energy yield as calculated by energy in ethanol converted from net energy content of the feed-stock. In contrast, cellulose-derived ethanol could have a 37% yield. Furthermore, cellulose and hemicellulose are the major components of plant cell walls and hence the largest components of all biomass. It is estimated that use of waste cellulose can displace 10% of current gasoline usage, and more gasoline usage can be displaced upon development of energy crops.

The current rate-limiting step to produce cellulose-derived ethanol is the degradation of cellulose and hemicellulose polymers to sugars. The rigid, crystalline structure of cellulose and its encasement by hemicellulose and other structural polymer such as lignin prevent the efficient breakdown into sugars. Biomass-degrading microbes and fungi are sources of enzymes to improve wood pre-processing and cellulose breakdown. Many anaerobic bacteria such as *Clostridium, Acetivibrio, Bacteroides* and *Ruminococcus* secrete a large extracellular enzyme complex named cellulosome, which is capable of degrading cellulose, hemicellulose and pectin (3, 4, 6, 9, 10). Understanding the molecular mechanisms of these microbial systems is essential for modeling, prediction and engineering of the optimized enzymes and microbes for efficient cellulose conversion.

Current efforts in understanding cellulose degradation by microbes largely focus on several Clostridia strains such as *Clostridium thermocellum* and *Clostridium cellulolyticum*. However, the functional studies at molecular level have been frustrated by the lack of efficient genetic tools in these microorganisms. For example, no expression vectors have been reported in *C. thermocellum*, no mutagenesis systems have been established, and gene transfer technology via electroporation is not straightforward. As to *C. cellulolyticum*, there is a lack of a targeted mutagenesis method. The only *C. cellulolyticum* mutants reported so far are spontaneous mutants generated by native transposes existing in the bacterial genome (7). Although it has been expected that some cellulosome components are essential for cellulosome integrity and function in *C. cellulolyticum*, this hypothesis is largely unproven due to lack of a targeted mutagenesis system. For the same reason, the regulatory systems of cellulosome production and secretion still remain largely unknown. Therefore, there is an urgent need to develop an efficient mutagenesis system for identifying structural and regulatory genes critical for cellulosome function.

SUMMARY OF THE INVENTION

The present invention provides a method of targeted mutagenesis in Gram-positive bacteria that employs a suicide integrative vector to genetically modify Gram-positive bacteria. The methodology of the present invention is not only useful for providing valuable information on the function of a gene of interest, but also for generating genetically modified bacteria useful for bioenergy production.

The present methodology is essentially applicable to mutating any target gene of interest in Gram-positive bacteria, including especially bacteria within the class Clostridia. Examples of bacteria within the class of Clostridia contemplated by the invention include celllulolytic bacteria such as species of *Clostridium*, e.g., *C. cellulolyticum*, and bacteria that are closely related to *C. cellulolyticum*.

In accordance with the present invention, effective targeted mutagenesis of Gram-positive bacteria can be achieved by employing a vector designed to be suicidal and integrative, i.e., a vector that does not replicate in a target Gram-positive bacterium and is capable of being integrated into the bacterial chromosome. Various elements of the vector that provide these desirable properties, including the replication origin, the targeting nucleotide sequence that mediates single crossover recombination between the vector and the target gene in the chromosome, and the overall size of the vector, are described in details hereinbelow. A preferred vector for use in the present invention is a vector which contains an internal fragment of a target gene wherein the fragment is cloned into a pKNOCK backbone. The present invention has demonstrated for the first time the successful use of a suicide integrative vector, generated by cloning an internal fragment of the Cel8C gene into the pKNOCK-Cm vector, in integration into the chromosomal Cel8C gene of a Gram-positive bacterium, specifically *C. cellulolyticum*, resulting in inactivation of the Cel8C gene.

Transformants which have had a successful integration event can be identified by one or a combination of several techniques. Such transformants form another embodiment of the present invention.

DETAILED DESCRIPTION OF THE INVENTION

The present invention provides a method of targeted mutagenesis in Gram-positive bacteria that effectively integrates a suicide vector into a target gene in the bacterial chromosome resulting in inactivation of the target gene.

In accordance with the present invention, effective targeted mutagenesis of Gram-positive bacteria has been made possible by employing a suicide integrative vector described hereinbelow. The present methodology is applicable to all Gram-positive bacteria, especially bacteria within the class Clostridia, which include but are not limited to, *Acetivibrio cellulolyticus*, *Clostridium acetobutylicum*, *Clostridium autoethangenum*, *Clostridium carboxidivorans*, *Clostridium celerecrescens*, *Clostridium cellobioparum*, *Clostridium cellulolyticum*, *Clostridium cellulovorans*, *Clostridium ljungdahlii*, *Clostridium papyrosolvens*, *Clostridium pasteurianum*, *Clostridium phytofermentans*, *Clostridium populeti*, *Clostridium saccharolyticum*, *Clostridium thermocellum*, *Thermoanaerobacter brockii* subsp. *Finnii*, *Thermoanaerobacter ethanolicus*, *Thermoanaerobacterium thermosaccharolyticum*, *Thermoanaerobacterium xylanolyticum*, and *Anaerocellum thermophilum*.

In a specific embodiment, the present method is directed to targeted mutagenesis of cellulolytic Gram-positive bacteria within the class of Clostridia, i.e., bacteria capable of hydrolyzing cellulose, hemicellulose or lignin into sugar. Examples of cellulolytic bacteria from the class Clostridia include *Clostridium autoethangenum*, *Clostridium carboxidivorans*, *Clostridium celerecrescens*, *Clostridium cellobioparum*, *Clostridium cellulolyticum*, *Clostridium cellulovorans*, *Clostridium ljungdahlii*, *Clostridium papyrosolvens*, *Clostridium pasteurianum*, *Clostridium phytofermentans*, *Clostridium populeti*, *Clostridium saccharolyticum*, and *Clostridium thermocellum*. In a preferred embodiment, the cellulolytic bacterium is *Clostridium cellulolyticum*.

According to the present invention, effective targeted mutagenesis of Gram-positive bacteria is achieved by employing a suicide integrative vector.

By "suicide integrative vector" it is meant that the vector does not replicate in the target Gram-positive bacterium to be mutagenized, but is capable of being integrated into the bacterial chromosome. The vector for use in the present method is typically a small circular double stranded DNA plasmid.

The vector for use in practicing the present invention is made "suicidal" by employing a replicon that is non-functional in the target Gram-positive bacterium, yet functional in a different host such that the vector can be propagated and amplified for use in the method of the present invention. For example, the γ-origin of replication (SEQ ID NO: 1) of the R6K plasmid (described by Kolter et al., *Cell* 15: 1199-1208 (1978)), which has activity only in those *E. coli* strains that can provide in trans the π protein encoded by the R6K plasmid, but does not have any activity in Gram-positive bacteria.

The vector for use in practicing the invention is made to have the capacity to integrate into the genome of a recipient bacterium by homologous recombination. The integration property of the vector is determined by including in the vector a targeting nucleotide sequence having a length and homology to a target gene of interest, sufficient to permit a single cross over recombination between the vector and the host chromosomal DNA which results in the integration and insertion of the entire vector into the target gene. Generally speaking, the targeting nucleotide sequence in the vector should contain at least 100 bp or 200 bp, preferably at least 400 bp, and more preferably at least 500 bp, in order to allow for efficient homologous recombination with host chromosome. Further, the targeting nucleotide sequence in the vector should have a sequence identity of at least 75%, preferably at least 85%, or more preferably at least 95% or even greater than 98% identity with the corresponding portion of the target gene to allow for efficient recombination. The frequency of single cross over recombination is believed to increase with increasing length and homology of the sequences. In certain preferred embodiments, the targeting nucleotide sequence in the vector is at least about 400 bp in length that shares at least about 95% identity with the target gene.

Figure 1A:
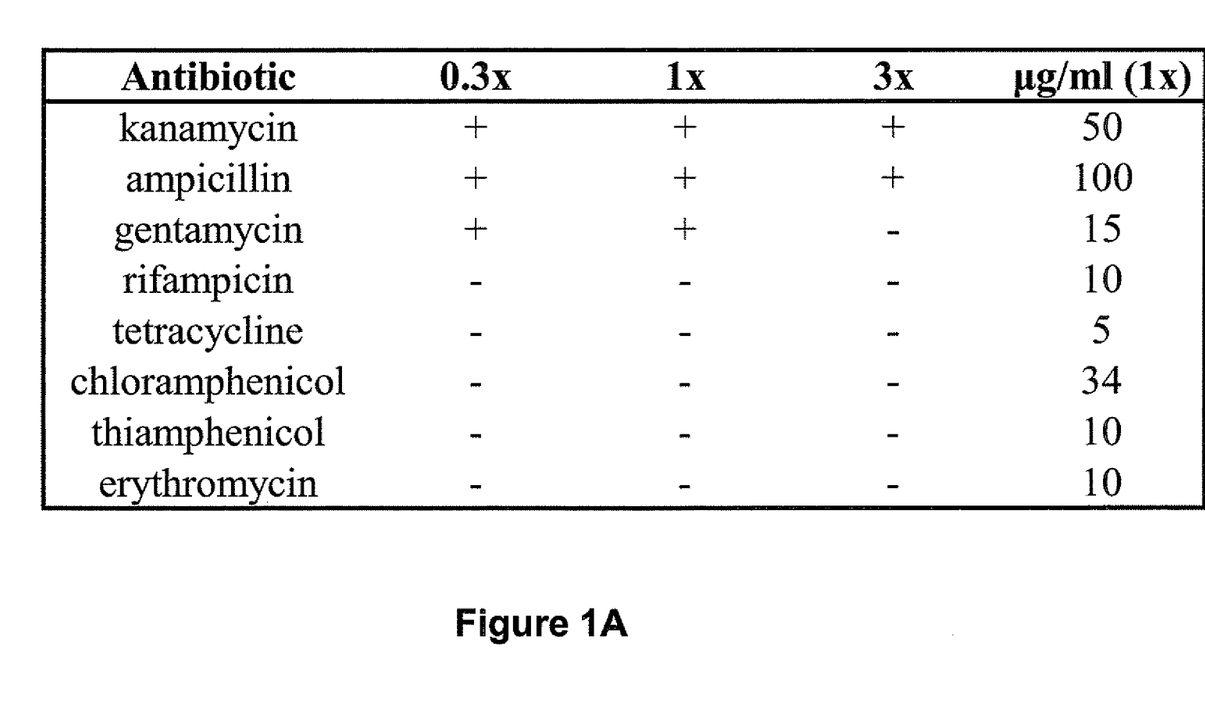
FIG. 1A. Antibiotic resistance Profiles of *C. cellulolyticum*. "+" and "−" represent positive and negative intrinsic antibiotic resistance, respectively.
Figure 1B:
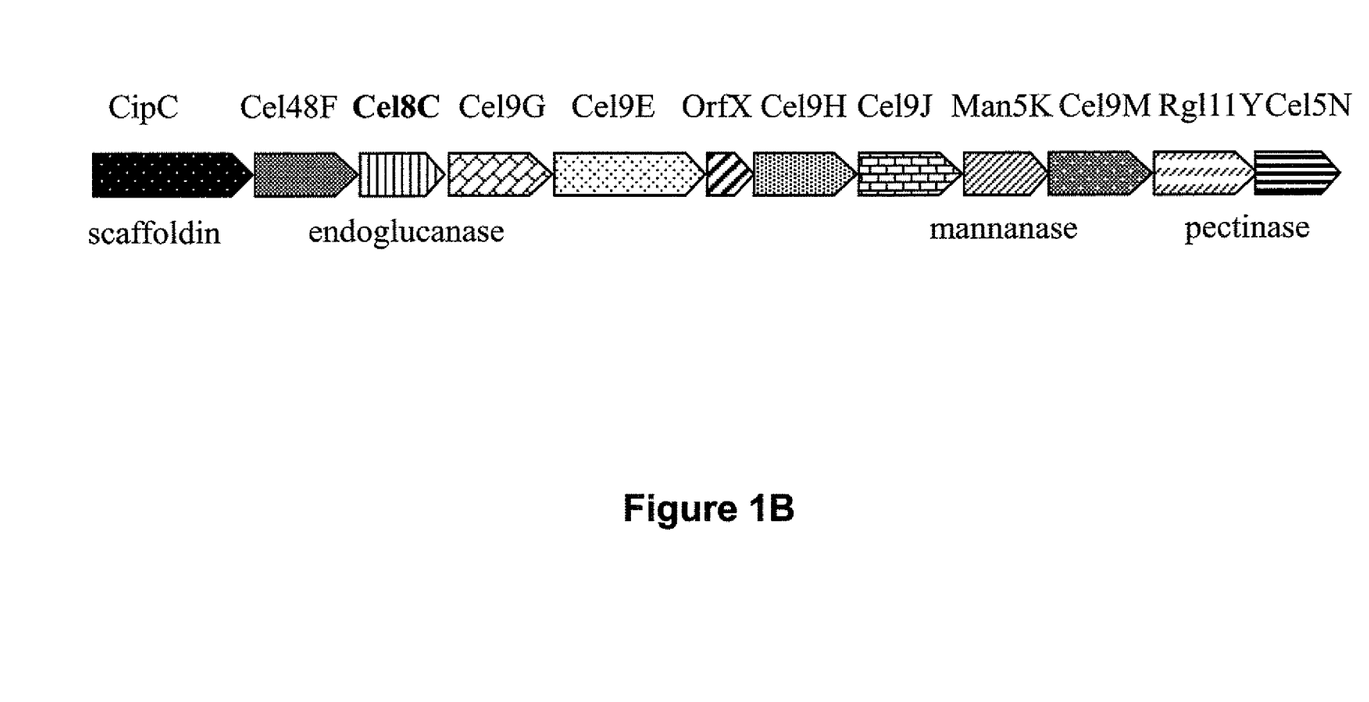
FIG. 1B. Genomic organization of the cel cluster of the cellulosomal genes.
Figure 1C:
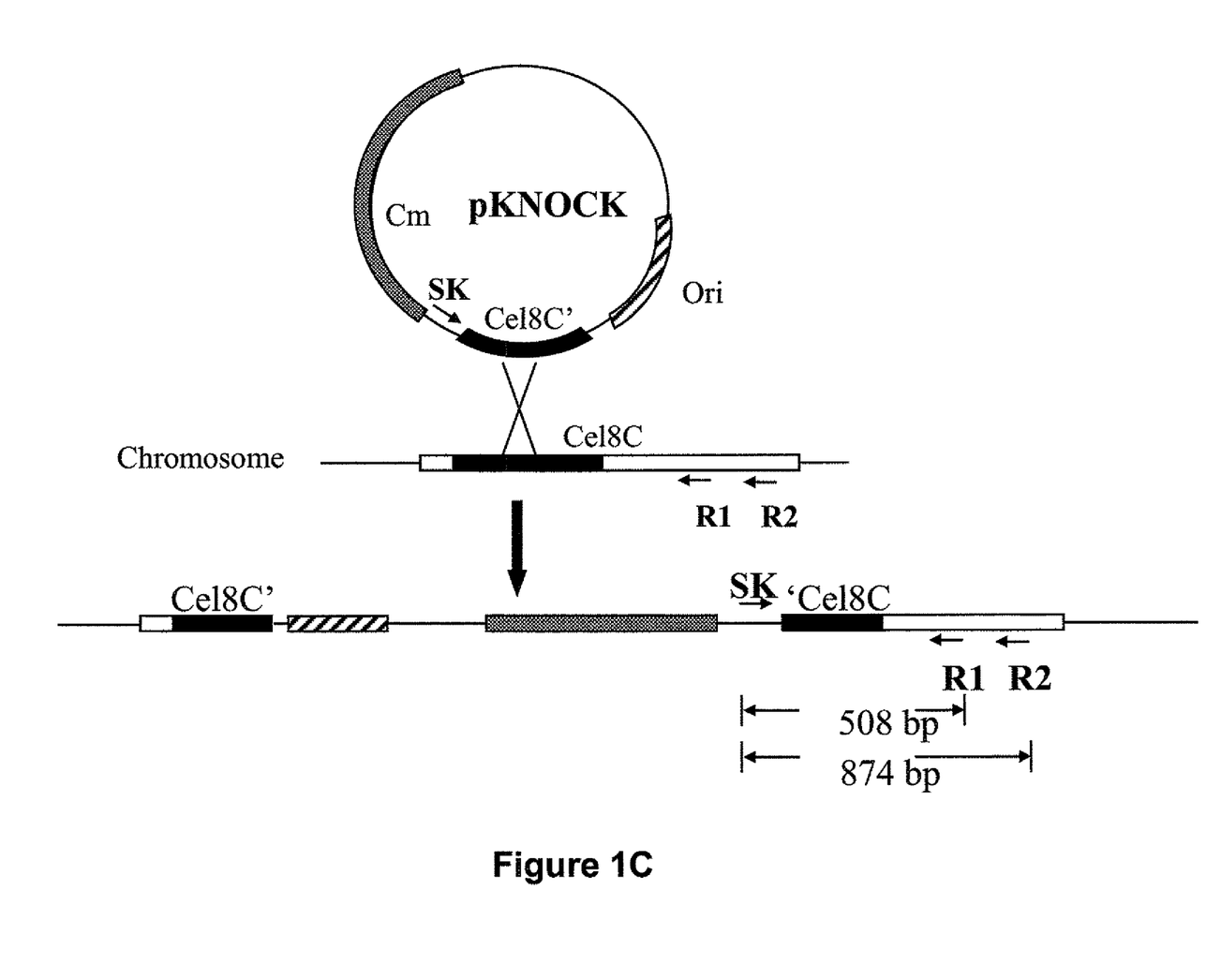
FIG. 1C. Scheme of insertional mutagenesis. Lines and boxes are not drawn to scale. Abbreviations: Ori, plasmid origin of replication; Cm, chloramphenicol; Cel8C' and 'Cel8C, truncated versions of Cel8C. SK, R1 and R2 are PCR primers.

The integration and insertion of the vector into the host chromosome results in two nucleotide sequences containing partial sequences of the target gene, intercepted by the vector sequence (illustrated in FIG. 1C). To ensure that the integration event inactivates the target gene, the targeting nucleotide sequence should be shorter in length than the targeting gene and correspond to only an internal part of the target gene, to ensure that neither of the two copies of the target gene resulting from the single cross over event produces or encodes a functional protein product. For example, as illustrated in FIG. 1C, even in the case where the targeting sequence in the vector shares 100% identity to an internal part of the target gene, the recombination event results in two mutant copies of the target gene, one copy lacks the 5' region and the other lacks the 3' region, which are separated by the vector sequence.

The present methodology is applicable to mutagenesis of any target gene, especially target genes in *Clostridium cellulolyticum*, the entire genomic sequence of which is available in GenBank under Accession No. NZ_AAVC000000000. Target genes of special interest include genes that encode cellulosome protein subunits (such as CipC, Cel48F, Cel8C, Cel9G, Cel9E, OrfX, Cel9H, Cel9J, Man5K, Cel9M, Rg11Y and Cel5N), genes that encode a metabolic enzyme such as pyruvate-ferredoxin oxidoreductase, NADPH-Fd oxidoreductase, NADH-Fd oxidoreductase, hydrogenase, lactate dehydrogenase, acetaldehyde dehydrogenase, alcohol dehydrogenase, phosphotransacetylase and acetate kinase, genes that encode proteins involved in sporulation, genes that encode an antiporter, and genes that encode regulatory proteins including DNA-binding transcription regulators.

The suicide integrative vector can be constructed to include a selectable or screenable genetic marker such as antibiotic markers. For example, as have been determined by the present invention, marker genes that confer resistance to gentamycin, rifampicin, tetracycline, chloramphenicol, thiamphenicol and erythromycin can be used in a suicide integrative vector for mutagenesis of *Clostridium cellulolyticum*.

The overall size of a suicide integrative vector should be such that permits the vector to have sufficient stability to allow for targeting and integration. In a preferred embodiment, the vector is about 2 kb in size. In other embodiments, the vector can be as small as 1.2-1.5 kb, and as large as 3-4 kb, or even 4-5 kb.

An especially preferred vector is made by cloning an internal part of a target gene into a pKNOCK vector backbone. pKNOCK vectors are small plasmids that contain the γ-origin of replication of the R6K plasmid, an antibiotic resistance gene of choice, and multiple unique restriction sites (1). The sequence of pKNOCK-Cm ("Cm" for chloramphenicol resistance gene) is set forth in SEQ ID NO: 2. A vector generated by cloning a fragment of Cel8C into the pKNOCK-Cm vector has been successfully integrated into the Cel8C gene of a Gram-positive bacterium, specifically *C. cellulolyticum*, resulting in inactivation of the Cel8C gene. It is believed that while the γ-origin of replication of the R6K plasmid is important for the success of pKNOCK-Cm, the antibiotic resistance gene (Cm) can be replaced with any other suitable antibiotic resistance genes such as chloramphenicol resistance gene, tetracyclin resistance gene, gentamycin resistance gene, kanamycin resistance gene, and ampicilin resistance gene, as well as a nutrition marker gene or nucleotide utilization gene, for example.

A suicide integrative vector can be introduced into a Gram-positive bacterium by known transformation techniques, such as electroporation, conjugation, DNA-calcium phosphate coprecipitation, general transduction, liposome fusion or protoplast transformation. Prior to introduction into a Gram-positive bacterium, the vector is preferably methylated for protection against restriction enzymes in the recipient bacterium. For example, the vector can be methylated using Msp methylase as described in Example 1 hereinbelow.

After transformation, transformants with the suicide integrative vector integrated in the chromosome can be selected by one or a combination of several routine techniques. In one embodiment, selection of transformants is based on the phenotype conferred by the selectable marker gene in the vector, such as antibiotic resistance, or ability to utilize a nucleotide, nucleotide analog, or a nutrient. In another embodiment, selection of transformants is based on a phenotype resulting from the inactivation of the target gene. For example, a disruption in the Cel8C gene has been shown in Example 2 to severely impair cellulosome activity and transformants having such a disruption failed to grown in medium with cellulose as the sole carbon source. In still another embodiment, transformants can be selected based on analysis of genomic DNA (e.g., Southern blot analysis or PCR) and confirmation of integration and insertion of the vector in the target location.

Strains generated by using the methods described herein, and the vectors designed for the practice of the present invention are all parts of the present invention.

This invention is further illustrated by the following examples, which are not to be construed in any way as imposing limitations upon the scope thereof. The terms and expressions which have been employed in the present disclosure are used as terms of description and not of limitation, and there is no intention in the use of such terms and expressions of excluding any equivalents of the features shown and described or portions thereof. It is to be understood that various modifications are possible within the scope of the invention. All the publications mentioned in the present disclosure are incorporated herein by reference.

EXAMPLE 1

Protocol for Insertional Mutagenesis in *Clostridium cellulolyticum*

This Example describes the general protocol which can be employed for insertional mutagenesis in *Clostridium cellulolyticum*, and was followed to obtain a stable Cel8C disruption mutant as further described in Example 2.

Generation of an Internal Fragment of the Target Gene Using PCR

PCR primers were designed to amplify an internal region (~500 bp in length) of the target gene. The PCR reaction proceeded in a final volume of 50 μl, which was prepared as follows.

35 μl Nuclease free H$_2$0
5 μl of 10×PCR buffer
3 μl of 25 mM MgCl$_2$
1 μl of dNTP's
1 μl of Taq polymerase
1 μl of genomic DNA
2 μl of primer 1 (2.5 μM)
2 μl of primer 2 (2.5 μM)

PCR was performed using the following programmed cycle of steps: 94° C. for 2 min., 35 cycles (94° C. for 30 sec, 60° C. for 30 sec, 72° C. for 60 sec, and 72° C. for 4 min, and the final product was maintained at 4° C. until further use.

Cloning the Internal Fragment into a Suicide Vector pKNOCK-Cm

Prior to inserting into a vector, the fragment may be further modified if necessary, by addition of adapters, linkers, or simply cleavage with restriction endonucleases, e.g., SmaI, to create the desired compatible ends for cloning into the vector.

The suicide backbone vector pKNOCK-chloramphenicol was linearized with the restriction endonuclease SmaI in a final volume of 100 μl (composed of 50 μl suicide plasmid pKNOCK Cm$^r$, 3 μl SmaI, 10 μl 10× buffer, and 37 μl nuclease-free H$_2$O). The digestion proceeded for about 2 hrs at about 25° C. or room temperature. The reaction was terminated by incubating the reaction mixture at about 70° C., followed by centrifugation to precipitate the vapor After cooling down the mixture on ice, 12 μl of a 10× buffer and 5 μl SAP ("Shrimp Alkaline Phosphatase") was added to the reaction mixture for incubation for 1.5 hour at 37° C. The reaction was terminated by incubating at 70° C. for 10 minutes, centrifuged, and the volume was adjusted by adding 60 μl water prior to extraction with 100 μl of phenol/chloroform. The aqueous phase was removed and adjusted by addition of 0.11 volumes of 3M sodium acetate and 3 volumes of ethanol, and the mixture was placed at −20° C. overnight. The mixture was then centrifuged in a table-top microcentrifuge for 20 min. at 14,000 rpm. The supernatant was removed and pellet washed with 70% ethanol. The pellet was eventually dried in a hood and suspended in water.

The PCR product can be purified using any commercially available PCR purification kit, or by standard ethanol precipitation methods. The PCR product and the SmaI phosphatased pKNOCK vector were ligated using the TA-Cloning Kit™ from Invitrogen™ based on the instructions provided by the manufacturer, and the resulting suicide vector-insert construct was purified in accordance with the instructions provided therein.

The suicide plasmid carrying a target gene fragment can be maintained in *E. coli* strains producing the lambda pir protein (JM 109/λpir, S17-1/λpir or B1255). Thawed competent cells of *E. coli* S17-1/λpir were thawed on ice for 5 minutes (about 40 μl). 1-2 μl of ligation was added to the cells, which were then incubated on ice for 5 minutes. The mixture was then transferred into a 2 mm gap sterile cuvette and a BTX set at a setting of 2.50 kV, 0 μf capacitance timing, and 129 resistance timing. 1 ml of SOC (SOC=SOPB+10 mM MgSO4+20 mM glucose) was immediately added to the electroporated cells, and the mixture was incubated at 37° C. for 45 minutes to one hour. Afterwards, the cells were collected by centrifugation and were plated on LB agar plates with chloramphenical or thiamphenicol (an analogue of chloramphenical) and incubated overnight. Colonies with insert were further characterized by PCR or sequencing.

In Vitro Methylation of pKNOCK Constructs

The resultant pKNOCK-insert construct was methylated by incubation with MspI in a total reaction volume of 100 μl (50 μl of plasmid, 2 μl of MspI, 10 μl of 10× buffer, 0.25 μl of 400×SAM, and 38 μl of nuclease-free H$_2$O) at 37° C. for two hours. The reaction was terminated by incubating the reaction mixture at 70° C. for 10 minutes, and the plasmid DNA was precipitated by using ethanol and sodium acetate, and was resuspended in H$_2$O.

Preparation of *Clostridium cellulolyticum* for Electroporation

Cells of *Clostridium cellulolyticum* ATCC 35319 were grown for 17-24 h in 50 ml cultures in VM medium until late exponential phase (OD600 of 0.5-1, 5×10$^6$ c.f.u./ml). The cells were centrifuged at about 4° C. in a Sorval RC5C centrifuge and resuspended in 10 ml ice-cold electroporation buffer (270 mM sucrose, 1 mM MgCl2, 5 mM sodium phosphate buffer, pH 7.4). The cells were precipitated by centrifugation and the cell pellet was washed with 10 ml ice-cold electroporation buffer, and resuspended in a total volume of 1 ml of the buffer. Resuspended cells were transferred to BTX Cuvette Model #620 (2 mm gap) and were incubated for 10 minutes on ice before electroporation.

Electroporation was performed in "HV" mode at a setting of 15 kV, 25 µF, and 48 ohms. Each cuvette contained about 200 µl cells and 1-2 µg of the pKNOCK construct. Cells were pulsed for 1.9-2.0 msec at a field strength of 7.5 kV/cm, and 1 ml of VM medium was immediately added to the cuvette after electroporation. The mixture was kept overnight at 34° C. The next day, cells were plated on VM plates containing 5 µg/ml thiamphenicol and kept at 34° C. for 1-2 weeks.

Growth of Mutant Candidates and Confirmation of Disruption

A single colony was picked and streaked onto fresh plates with 5 µg/ml thiamphenicol, and incubated anaerobically at 34° C. for 1-2 weeks. A single colony was picked from this plate and inoculated into 1 ml VM medium with 5 µg/ml thiamphenicol. The plates were incubated anaerobically at 34° C. The culture became cloudy in about 7 days. An aliquot of about 0.5 ml were then added to 10 ml VM medium with 5 µg/ml thiamphenicol, and incubated anaerobically at 34° C. The culture was cloudy in 3-7 days.

Genomic DNA was extracted from 5 ml of the culture and used as template for PCR verification or Southern blotting.

VM-Medium

The VM medium was derived from GS medium (5) by replacing yeast extract with the following Vitamin solution:

| 0.08 uM | Biotin |
|---|---|
| 0.02 uM | Pyridoxamine |
| 0.001 Um | Cyanocobalamin |
| 0.15 uM | p-aminobenzoic acid |
| 0.9 uM | Thiamin |
| 0.22 uM | L-alanine |
| KH$_2$PO$_4$ | 1.5 g |
| K$_2$HPO$_4$ | 2.9 g |
| Urea | 2.14 g |
| MgCl$_2$•6H$_2$O | 1.0 g |
| CaCl$_2$•H$_2$O | 0.15 g |
| FeSO$_4$•6H$_2$O | 1.25 mg |
| Cysteine-HCl | 1.0 g |
| Yeast extract | 6.0 g |
| Resazurin | 2.0 mg |
| MOPS | 20.9 g |
| Cellobiose | 5.1345 g (15 mM)* |
| Final volume | 1 Liter |

PH 7.5, after autoclaving, the pH was 7.4

All ingredients were added except cellobiose and vitamins before autoclaving. Original GS media contained 10 g/L cellobiose. The generation time in this media was approximately 6 h at 34° C. The medium can be solidified with 1.5% agar as appropriate.

Modifications of VM to Reduce Phosphate Precipitate

| KH$_2$PO$_4$ | 1.0 g |
|---|---|
| K$_2$HPO$_4$ | 3.4 g |
| Urea | 2.14 g |
| MgCl$_2$•6H$_2$O | 1.0 g |
| CaCl$_2$•H$_2$O | 0.15 g |
| FeSO$_4$•6H$_2$O | 1.25 mg |
| Cysteine-HCl | 1.0 g |
| Resazurin | 2.0 mg |
| MOPS | 20.9 g |
| Vitamins | 10 ml of 100X |
| Cellobiose | 50 ml of 20X (5.1345 g or 15 nM) |
| Final volume | 1 Liter |

PH ~6.2

EXAMPLE 2

Generation of *Clostridium cellulolyticum* cel8C Mutant

To determine the appropriate antibiotics for selection of genetically modified *C. cellulolyticum* strains, the native antibiotic resistance characteristics of *C. cellulolyticum* were assessed. 3 µl actively grown *C. cellulolyticum* ATCC 35319 cells were diluted 1:100 in a defined medium VM (5) containing a range of antibiotics of different concentrations. Cells were incubated at 34° C. for seven days with occasional agitation and the growth was monitored by measuring optical densities every hour with a BioScreen C machine (Oy Growth Curves Ab Ltd). The results indicated that *C. cellulolyticum* was sensitive for rifampicin, tetracycline, chloramphenicol/thiamphenicol, erythromycin and gentamycin (FIG. 1A).

Figure 1D:
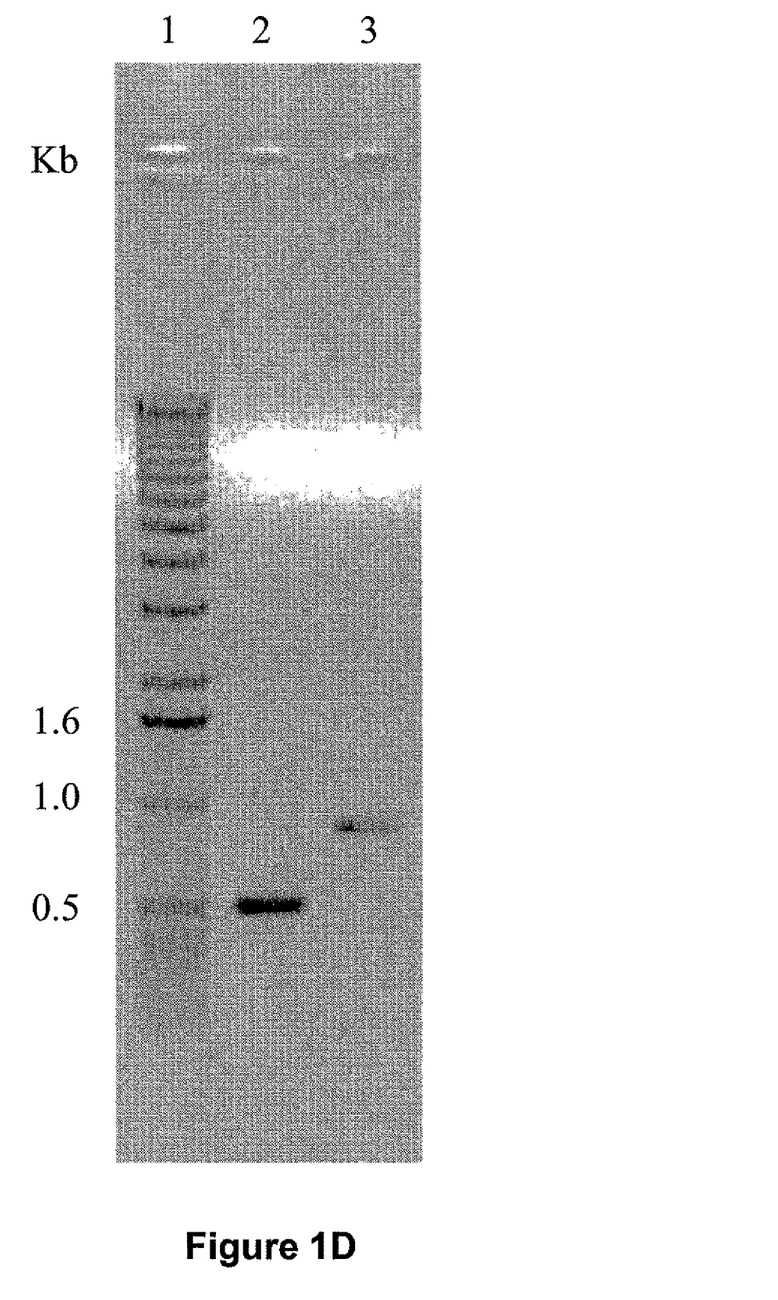
FIG. 1D. Agarose electrophoresis to examine PCR products using genomic DNA template prepared from the mutant. Lane 1: DNA ladder; lane 2: PCR product with primers SK+R1; lane 3: PCR product with primers SK+R2.
Figure 1E:
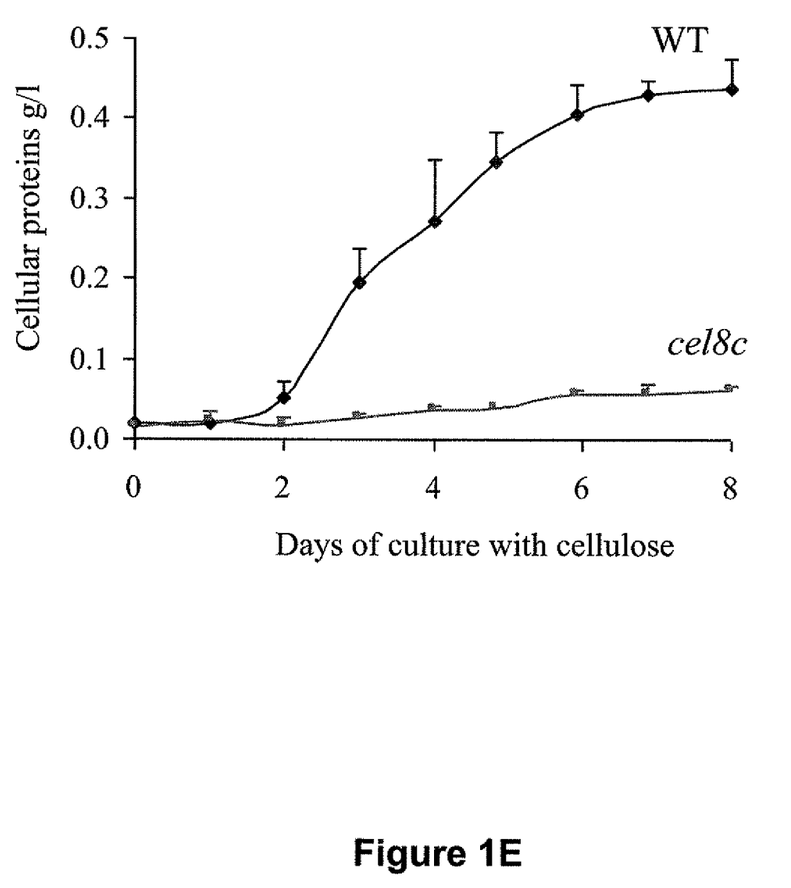
FIG. 1E. Growth of the wild-type and mutant strain in liquid VM medium containing 7.5 g/l cellulose. Growth was estimated by measuring the cellular proteins.

Subsequently the cellulosome subunit, Cel8C, was targeted for disruption in the genome according to the protocols described in Example 1. As shown in FIG. 1B, disruption of Cel8C was expected to have polar effects to other cellulosome subunits located immediately downstream of the Cel8 locus and thus severely impair or even completely abolish cellulosome activity, providing easy phenotypes for detection. The scheme of insertion mutagenesis is described in FIG. 1C. In short, an internal fragment of Cel8C (nucleotides #283-720 bp of Cel8C, as set forth in SEQ ID NO: 3) was amplified from the genome by PCR. The blunt ended DNA fragment was subcloned into a Sma I site of the suicidal vector pKNOCK-Cm (1), the entire sequence of which is set forth in SEQ ID NO: 2). The integrity and orientation of the insert was identified by DNA sequencing of the plasmid with SK and KS primers flanking multiple cloning sites. Next, the suicidal construct, i.e., pKNOCK which incorporated the Cel8C fragment, was transformed into *C. cellulolyticum* by electroporation under anaerobic conditions according to the protocol described in Example 1. Since *C. cellulolyticum* synthesizes a restriction enzyme CceI to degrade foreign DNA, the plasmid was methylated with Msp I methylase (New England Biolabs) for protection prior to transformation. After two weeks of incubation at 34° C. in an anaerobic chamber, colonies appeared on a solid VM medium containing cellobiose as the sole carbon and energy source and 5 µg/ml thiamphenicol for antibiotics selection. The colonies were restreaked onto fresh VM plates with thamphenicol, and subsequently single colonies were picked and grown in liquid VM medium with thamphenicol to obtain a large amount of biomass. Genomic DNA was extracted using a genomic DNA extraction kit (Promega) and used as template in PCR amplifications with a vector-specific primer (SK) and gene-specific primers (R1 and R2). Single, sharp PCR bands were generated at expected sizes (FIG. 1D). Further sequencing of PCR products confirmed that the suicidal plasmid was integrated into the correct site of the genome. In addition, the disruption of the Cel8C locus in the genome was also confirmed by Southern blot analysis. As expected, 4.3 kb and 2.3 kb bands were observed for 5 μg of HindIII digested genomic DNA of the wild-type and mutant strains, respectively. Finally, the cel8C mutant was examined for its capacity to grow in VM with cellulose as the sole carbon and energy source. The same number of cells from the wild-type *C. cellulolyticum* and cel8C mutant were washed twice and resuspended in fresh VM medium, and inoculated into 100 ml VM medium containing 7.5 g/l cellulose. After 10 days of incubation at 34° C., the mutant failed to show significant growth, while the wild-type *C. cellulolyticum* reached stationary phase (FIG. 1E). This result serves as in vivo physiological evidence for the disruption of Cel8C.

REFERENCES

1. Alexeyev, M. F. 1999, The pKNOCK series of broad-host-range mobilizable suicide vectors for gene knockout and targeted DNA insertion into the chromosome of gram-negative bacteria. Biotechniques 26:824-6, 828.
2. Desvaux, M. 2005. The cellulosome of *Clostridium cellulolyticum*. Enzyme and Microbial Technology 37:373-85.
3. Ding, S. Y., E. A. Bayer, D. Steiner, Y. Shoham, and R. Lamed. 1999. A novel cellulosomal scaffoldin from *Acetivibrio cellulolyticus* that contains a family 9 glycosyl hydrolase. J Bacteriol 181:6720-9.
4. Ding, S. Y., E. A. Bayer, D. Steiner, Y. Shoham, and R. Lamed. 2000. A scaffoldin of the *Bacteroides* cellulosolvens cellulosome that contains 11 type II cohesins. J Bacteriol 182:4915-25.
5. Garcia-Martinez, D. V., Shinmyo, A. Madia, A. and Demain. A. L. 1980. Studies on cellulase production by *Clostridium thermocellum*. Eur J Appl Microbiol Biotechnol 9, 189-197.
6. Jennert, K. C., C. Tardit D. I. Young, and M. Young. 2000. Gene transfer to *Clostridium cellulolyticum* ATCC 35319. Microbiology 146 Pt 12:3071-80.
7. Lamed, R., and E. A. Bayer. 1988. Cellulosome from *Clostridium thermocellum*. Methods Enzymol. 160:472-81.
8. Maamar, H., O. Valette, H. P. Fierobe, A. Belaich, J. P. Belaich, and C. Tardif. 2004. Cellulolysis is severely affected in *Clostridium cellulolyticum* strain cipCMut1. Mol Microbiol 51:589-98.
9. Office of Science, U.S.D.o.E. 2005. Missions Overview: The role of microbial systems in energy production, environmental remediation and carbon cycling and sequetration, DOE Genomics: GTL Roadmap.
10. Ohara, H., S. Karita, T. Kimura, K. Sakka, and K. Ohmiya. 2000. Characterization of the cellulolytic complex (cellulosome) from *Ruminococcus albus*. Biosci Biotechnol Biochem 64:254-60.
11. Pages, S., A. Belaich, J. P. Belaich, E. Morag, R. Lamed, Y. Shoham, and E. A. Bayer. 1997. Species-specificity of the cohesin-dockerin interaction between *Clostridium thermocellum* and *Clostridium cellulolyticum*: prediction of specificity determinants of the dockerin domain. Proteins 29:517-27.
12. Perret, S., H. Maamar, J. P. Belaich, and C. Tardif. 2004. Use of antisense RNA to modify the composition of cellulosomes produced by *Clostridium cellulolyticum*. Mol Microbiol 51:599-607.
13. Tardif, C., H. Maamar, M. Balfin, and J. P. Belaich. 2001. Electrotransformation studies in *Clostridium cellulolyticum*. J Ind Microbiol Biotechnol 27:271-4.
14. Tummala, S. B., N. E. Welker, and E. T. Papoutsakis. 1999. Development and characterization of a gene expression reporter system for *Clostridium acetobutylicum* ATCC 824. Appl Environ Microbiol 65:3793-9.

What is claimed is:

1. A method of targeted mutagenesis in a Gram-positive bacterium within the class of Clostridia, comprising:
   providing a suicide integrative vector, wherein said vector is methylated and comprises: the γ-origin of replication of the R6K plasmid (SEQ ID NO:1); a selectable marker gene; and a targeting nucleotide sequence having a length of at least 200 base pair and sequence identity of at least 75% with a target gene in the chromosome of said bacterium sufficient to permit homologous recombination and integration of said vector into said target gene, wherein integration of said vector into said target gene results in inactivation of said target gene;
   introducing said vector into cells of said bacterium; and
   selecting for cells in which said vector has integrated into said target gene.

2. The method of claim 1, wherein said Gram-positive bacterium is selected from the group consisting of *Acetivibrio cellulolyticus, Clostridium acetobutylicum, Clostridium autoethangenum, Clostridium carboxidivorans, Clostridium celerecrescens, Clostridium cellobioparum, Clostridium cellulolyticum, Clostridium eellulovorans, Clostridium ljungdahlii, Clostridium papyrosolvens, Clostridium pasteurianum, Clostridium phytofermentans, Clostridium populeti, Clostridium saccharolytieum, Clostridium thermocellum, Thermoanaerobacter brockii* subsp. *Finnii, Thermoanaerobacter ethanolicus, Thermoanaerobacterium thermosaccharolyticum, Thermoanaerobacterium xylanolyticum* and *Anaerocellum thermophilum*.

3. The method of claim 1, wherein said Gram-positive bacterium is selected from the group consisting of *Clostridium autoethangenum, Clostridium carboxidivorans, Clostridium celerecrescens, Clostridium cellobioparum, Clostridium cellulolyticum, Clostridium cellulovorans, Clostridium ljungdahlii, Clostridium papyrosolvens, Clostridium pasteurianum, Clostridium phytofermentans, Clostridium populeti, Clostridium saccharolytieum* and *Clostridium thermocellum*.

4. The method of claim 3, wherein said bacterium is *Clostridium cellulolyticum*.

5. The method of claim 1, wherein said targeting nucleotide sequence comprises at least about 400 nucleotides.

6. The method of claim 1, wherein said targeting nucleotide sequence is about 500 nucleotides in length.

7. The method of claim 1, wherein said targeting nucleotide sequence is at least about 85% identical to said target gene.

8. The method of claim 1, wherein said targeting nucleotide sequence is at least about 95% identical to said target gene.

9. The method of claim 1, wherein said target gene encodes a cellulosome protein.

10. The method of claim 1, wherein said target gene encodes a metabolic enzyme.

11. The method of claim 1, wherein said target gene encodes an antiporter, a protein involved in sporulation, or a transcription regulatory protein.

12. The method of claim 1, wherein said vector further comprises a nucleic acid encoding a selection marker that confers a selectable phenotype in said bacterium.

13. The method of claim 12, wherein said marker allows for selection based on antibiotic resistance, nucleotide or nucleotide analog, or nutrient requirement.

14. The method of claim 1, wherein said vector is a pKNOCK vector.

15. The method of claim 1, wherein said vector is introduced into said bacterium by electroporation.

16. The method of claim 1, wherein said vector is introduced into said bacterium by the group consisting of conjugation, DNA-calcium phosphate co-precipitation, general transduction, liposome fusion and protoplast transformation.

17. The method of claim 1, wherein said selecting is based on the phenotype conferred by a selectable marker gene in said vector.

18. The method of claim 1, wherein said selecting is based on a phenotype resulting from the inactivation of said target gene.

19. The method of claim 1, wherein said selecting is based on analysis of chromosomal DNA of said bacterium.

* * * * *

SEQUENCE LISTING

<160> NUMBER OF SEQ ID NOS: 3

<210> SEQ ID NO 1
<211> LENGTH: 779
<212> TYPE: DNA
<213> ORGANISM: Artificial Sequence
<220> FEATURE:
<223> OTHER INFORMATION: Synthetic nucleic acid (gamma-origin of
      replication)

<400> SEQUENCE: 1

```
cacgcgtcaa ttcgagggggg atcaattccg tgataggtgg gctgcccttc ctggttggct      60
tggtttcatc agccatccgc ttgccctcat ctgttacgcc ggcggtagcc ggccagcctc     120
gcagagcagg attcccgttg agcaccgcca ggtgcgaata agggacagtg aagaaggaac     180
acccgctcgc gggtgggcct acttcaccta tcctgcccgg ctgacgccgt tggatacacc     240
aaggaaagtc tacacgaacc ctttggcaaa atcctgtata tcgtgcgaaa aaggatggat     300
ataccgaaaa aatcgctata atgacccgga agcagggtta tgcagcggaa aacggaattg     360
atccggccac gatgcgtccg gcgtagagga tctgaagatc agcagttcaa cctgttgata     420
gtacgtacta agctctcatg tttcacgtac taagctctca tgtttaacgt actaagctct     480
catgtttaac gaactaaacc ctcatggcta acgtactaag ctctcatggc taacgtacta     540
```

```
agctctcatg tttcacgtac taagctctca tgtttgaaca ataaaattaa tataaatcag    600
caacttaaat agcctctaag gttttaagtt ttataagaaa aaaaagaata tataaggctt    660
ttaaagcttt taaggtttaa cggttgtgga caacaagcca gggatgtaac gcactgagaa    720
gcccttagag cctctcaaag caattttgag tgacacagga acacttaacg gctgacatg     779
```

<210> SEQ ID NO 2
<211> LENGTH: 1862
<212> TYPE: DNA
<213> ORGANISM: Artificial Sequence
<220> FEATURE:
<223> OTHER INFORMATION: Synthetic nucleic acid (pKNOCK-Cm vector)

<400> SEQUENCE: 2

```
ggggatcaat tccgtgatag gtgggctgcc cttcctggtt ggcttggttt catcagccat     60
ccgcttgccc tcatctgtta cgccggcggt agccggccag cctcgcagag caggattccc    120
gttgagcacc gccaggtgcg aataagggac agtgaagaag gaacacccgc tcgcgggtgg    180
gcctacttca cctatcctgc ccggctgacg ccgttggata caccaaggaa agtctacacg    240
aacccttggg caaaatcctg tatatcgtgc gaaaaaggat ggatataccg aaaaaatcgc    300
tataatgacc ccgaagcagg gttatgcagc ggaaaacgga attgatccgg ccacgatgcg    360
tccggcgtag aggatctgaa gatcagcagt tcaacctgtt gatagtacgt actaagctct    420
catgtttcac gtactaagct ctcatgttta acgtactaag ctctcatgtt taacgaacta    480
aaccctcatg gctaacgtac taagctctca tggctaacgt actaagctct catgtttcac    540
gtactaagct ctcatgtttg aacaataaaa ttaatataaa tcagcaactt aaatagcctc    600
taaggtttta agttttataa gaaaaaaaag aatatataag gcttttaaag cttttaaggt    660
ttaacggttg tggacaacaa gccagggatg taacgcactg agaagccctt agagcctctc    720
aaagcaattt tgagtgacac aggaacactt aacggctgac atgggaattc ccctccaccg    780
cggtggcggc cgctctagaa ctagtggatc ccccgggctg caggaattcg atatcaagct    840
tatcgatacc gtcgacctcg aggggggggcc cggtaccgag gacgcgtgtc gaataaaata    900
cctgtgacga agatcactt cgcagaataa ataaatcctg gtgtccctgt tgataccggg    960
aagccctggg ccaacttttg gcgaaaatga cgttgatc ggcacgtaag aggttccaac     1020
tttcaccata atgaaataag atcactaccg ggcgtatttt ttgagttatc gagattttca    1080
ggagctaagg aagctaaaat ggagaaaaaa atcactggat ataccaccgt tgatatatcc    1140
caatggcatc gtaaagaaca ttttgaggca tttcagtcag ttgctcaatg tacctataac    1200
cagaccgttc agctggatat tacggccttt ttaaagaccg taaagaaaaa taagcacaag    1260
ttttatccgg cctttattca cattcttgcc cgcctgatga atgctcatcc ggaatttcgt    1320
atggcaatga agacggtga gctggtgata tgggatagtg ttcacccttg ttacaccgtt    1380
ttccatgagc aaactgaaac gttttcatcg ctctggagtg aataccacga cgatttccgg    1440
cagtttctac acatatattc gcaagatgtg gcgtgttacg gtgaaaacct ggcctatttc    1500
cctaaagggt ttattgagaa tatgtttttc gtctcagcca atccctgggt gagtttcacc    1560
agttttgatt taaacgtggc caatatggac aacttcttcg ccccgttttt caccatgggc    1620
aaatattata cgcaaggcga caaggtgctg atgccgctgg cgattcaggt tcatcatgcc    1680
gtttgtgatg gcttccatgt cggcagaatg cttaatgaat tacaacagta ctgcgatgag    1740
tggcagggcg gggcgtaatt ttttttaaggc agttattggt gcccttaaac gcctggtgct    1800
```

```
acgcctgaat aagtgataat aagcggatga atggcagaaa ttcggacacg cgtcaattcg    1860
ag                                                                  1862

<210> SEQ ID NO 3
<211> LENGTH: 438
<212> TYPE: DNA
<213> ORGANISM: Artificial Sequence
<220> FEATURE:
<223> OTHER INFORMATION: Synthetic nucleic acid (Cel8C internal
      fragment)

<400> SEQUENCE: 3
caataatctc aactgccatc gcttcaagtg cagctgatca aattcctttc ccatatgacg     60
caaaatatcc aaatggagct tacagttgtc tggcggatag tcagtcaatc ggaaataatt    120
tagttcgcag tgaatgggaa cagtggaaaa gtgcacatat tacatcaaat ggagcaagag    180
gctataaaag agtccagaga gacgcaacta caaactatga tacggtttct gaaggacttg    240
gatacggttt gctgctttca gtttactttg gagaacaaca attatttgac gatttatatc    300
gctatgttaa agtattttta aattcgaacg gacttatgtc ctggcgtatt gactccagcg    360
gaaatataat gggaaaagac agtattggtg ccgcaacaga tgcagatgaa gatattgcgg    420
tatcccttgt gtttgctc                                                  438
```